United States Patent [19]

Katsuma et al.

[11] 4,346,973
[45] Aug. 31, 1982

[54] FOCUSING SCREEN INTERCHANGING DEVICE IN SINGLE LENS REFLEX CAMERA

[75] Inventors: Makoto Katsuma, Yokohama; Masayuki Suzuki, Tokyo; Kenichi Shinbori, Yokohama; Hiroyasu Murakami, Tokyo, all of Japan

[73] Assignee: Canon Kabushiki Kaisha, Tokyo, Japan

[21] Appl. No.: 230,272

[22] Filed: Jan. 30, 1981

[30] Foreign Application Priority Data

Jan. 31, 1980 [JP] Japan ................................ 55-12929
Jul. 8, 1980 [JP] Japan ................................ 55-93006
Jul. 9, 1980 [JP] Japan ................................ 55-93712

[51] Int. Cl.³ ........................ G03B 13/00; G03B 19/12
[52] U.S. Cl. ..................................... 354/152; 354/200
[58] Field of Search ................. 354/53, 152, 155, 289, 354/199, 200, 201, 219, 224, 225

[56] References Cited

U.S. PATENT DOCUMENTS

| | | | |
|---|---|---|---|
| 3,174,417 | 3/1965 | Sauer et al. | 354/219 UX |
| 4,132,472 | 1/1979 | Urano et al. | 354/53 X |
| 4,180,311 | 12/1979 | Urano et al. | 354/155 X |
| 4,187,016 | 2/1980 | Ishizaka | 354/200 X |

*Primary Examiner*—Donald A. Griffin
*Attorney, Agent, or Firm*—Toren, McGeady & Stanger

[57] ABSTRACT

In a single lens reflex camera a focusing screen is removably attached with a focusing screen fitting member unitarily formed therewith for fitting the focusing screen in the camera body with a spring being provided therebetween to form a focusing screen unit. The focusing screen fitting member is provided with a clamp holder portion for engagement with an interchanging tool for use in attaching and detaching the focusing screen unit to and from the camera body, whereby the interchanging operation of the focusing screen may be performed with ease and safety.

10 Claims, 28 Drawing Figures

FOCUSING SCREEN INTERCHANGING DEVICE IN SINGLE LENS REFLEX CAMERA

BACKGROUND OF THE INVENTION

1. Field of the Invention

This invention relates to a focusing screen interchanging device in single lens reflex cameras, and more particularly to the construction of a focusing screen and a fixture member therefor to be fitted in camera body in the form of a unit so that the attachment of the focusing unit to the camera body is made easy and safe to perform without contamination.

2. Description of the Prior Art

When it is desired to interchange the focusing screen in a single lens reflex camera, two methods have been put into practice in the past. One involves a removable finder housing containing a pentaprism which is attached to the camera body to make it possible to interchange the focusing screen through an opening provided in the top panel of the camera housing. The other involves application to a camera with a fixed finder housing wherein the interchanging of the focusing screen is performed through an opening in the amount on which the interchangeable objective lens is later to be attached.

Figure 1:
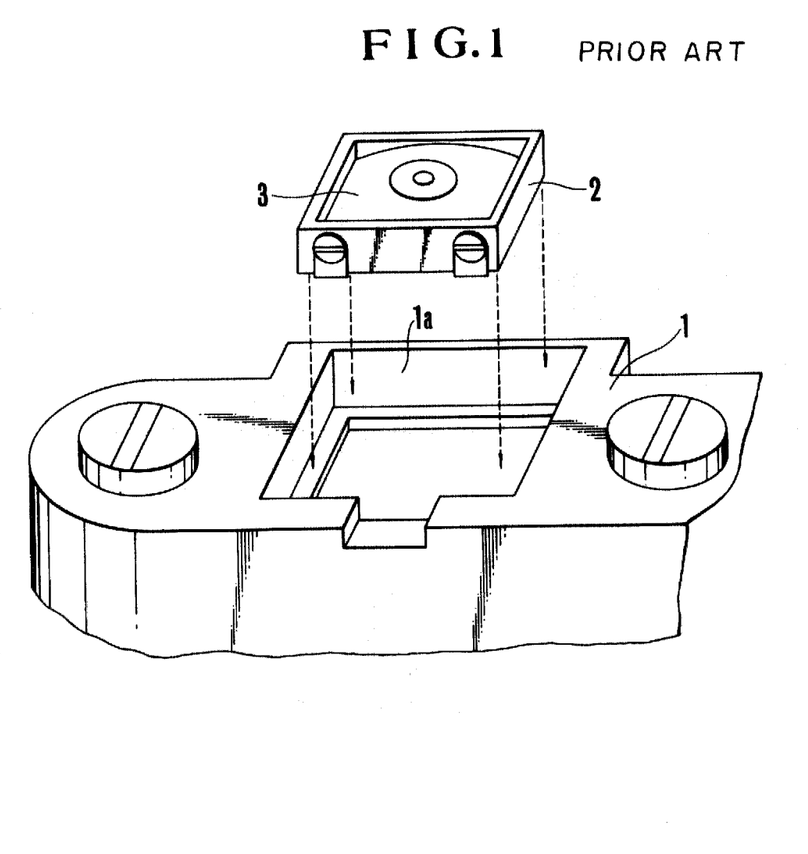
FIG. 1 is a perspective view of a conventional focusing screen interchanging device in a type of camera in which a removable finder-pentaprism is attached.

The former of the above-described interchanging methods has found use in the conventional type of focusing screen interchanging device an example of which is shown in FIG. 1 constructed as a unitary member with a focusing screen 3 and a fixture member 2. When it is desired to attach this to the camera body, the unit it placed into a receptor 1a within the interior of the camera housing 1. To detach the focusing screen 3, the operator must either pull out the focusing screen unit (comprising the above-described focusing screen 3 and the focusing screen fixture member 2) from the receptor 1a or turn the camera body 1 upside down, thus causing the focusing screen unit to fall out of the receptor 1a. Such a form of the device, however, requires not only difficult handling of the focusing screen during attaching and detaching operation, or when interchanging the unit, but also requires the operator to directly touch the focusing screen unit with his fingers, thereby producing a disadvantage in that either or both of the Fresnel and matted surfaces of the focusing screen is or are very often contaminated by finger prints, or scratched with the result that the finger optical system and light metering system malfunction.

Figure 2:
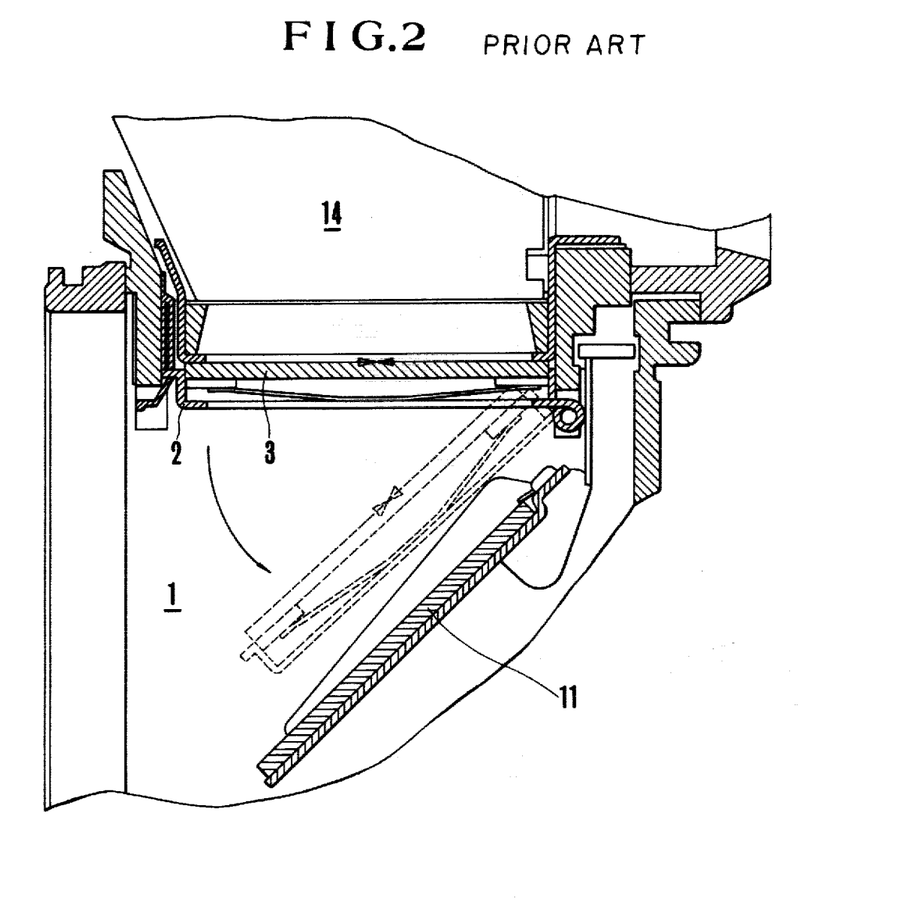
FIG. 2 is a sectional view of a conventional focusing screen interchanging device in another type of camera in which the focusing screen is dealt with through the opening of the mount for the objective lens.

The latter method of handling the focusing screen through the opening in the lens mount also applies to a conventional type of device, an example of which is shown in FIG. 2, where the focusing screen 3 only is made interchangeable as is common practice in the prior art, while the fixture member 2 for the focusing screen 3 is pivotally mounted on the framework of the camera body 1. When the focusing screen is to be attached, this member 2 is turned to a position shown by dashed lines, then the focusing screen 3 is put on the fixture member 2 by the use of tweezers or the like, and then the fixture member 2 with the focusing screen 3 thereon is returned to the operative position shown by the solid lines by a finger of the operator. Since, however, the focusing screen 3 is generally made of a plastic plate very susceptible to scratches, such method gives rise to a very difficult problem that the fixture member 2 is imparted with a rigidity strong enough to assure the accurate fitting of the focusing screen 3 under the bottom face of the pentaprism 14 within the camera housing 1 at a certain position without causing the mechanical complexity to be increased. Further, the use of the finger in moving the focusing screen fixture member 3 to the prescribed position and clamping it therein leads to a high possibility of occurrence of a finger print or scratches on or in the focusing screen 3 and the mirror 11 which also produce bad influence on the light metering system and the view-field of the finder. Another disadvantage is that the focusing screen 3 is liable to be broken by mishandling when interchanged so that the required precision of fixture of the focusing screen cannot often be reproduced. Still another disadvantage is that when the necessity of repairing or exchanging the focusing screen fixture member 2 with a new one arises, it entails great cost, and reestablishment of the original precision after the reassembly operation is very difficult to achieve.

SUMMARY OF THE INVENTION

The present invention is intended to eliminate the above-described drawbacks of the conventional device, and has for its object to provide a focusing screen interchanging device in a single lens reflex camera which comprises a focusing screen unit consisting of a focusing screen and a fixture member therefor, and an interchanging tool with the advantage that as the focusing screen unit is attached to and detached from the camera body through the interchanging tool, the interchanging of the focusing screen is achieved with ease and without causing any damage of the focusing screen by finger prints and scratches which would be otherwise caused during attachment and detachment.

Another object of the present invention is to provide a focusing screen interchanging device of the character described above with the focusing screen unit and interchanging tool being adapted particularly to the type of single lens reflex camera where the focusing screen is dealt with through the opening in the mount for the objective lens when it is interchanged.

DETAILED DESCRIPTION OF THE PREFERRED EMBODIMENTS

Figure 3:
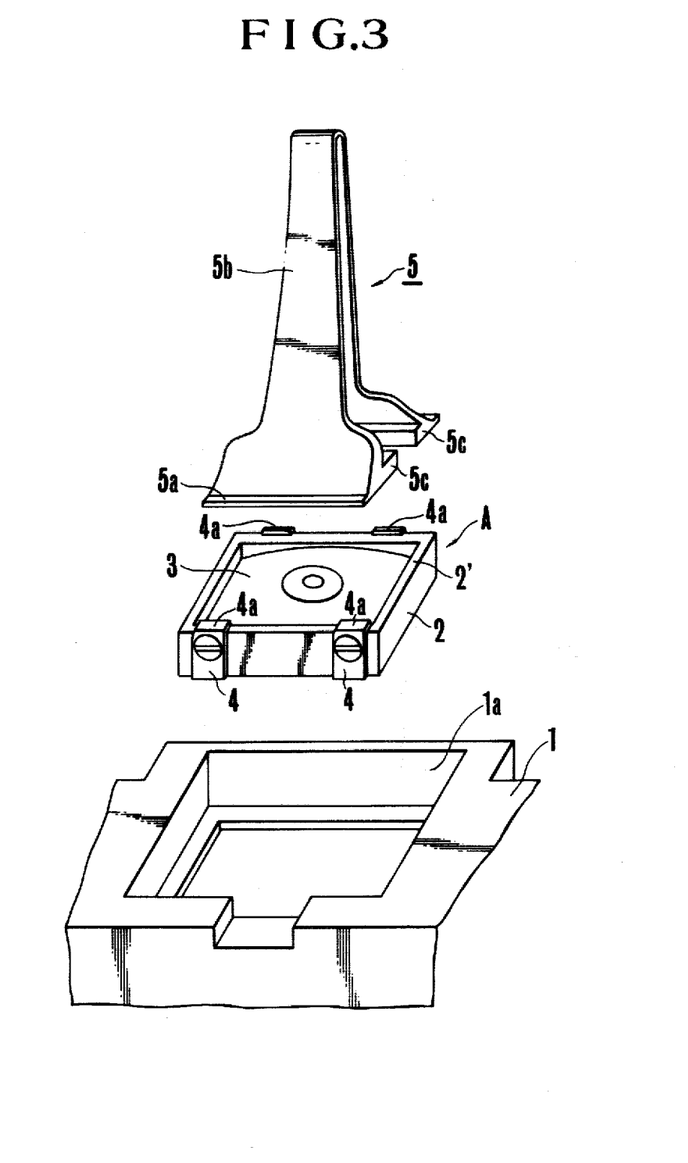
FIG. 3 is a perspective view of one embodiment of a focusing screen interchanging device according to the present invention applied to the type of camera whose pentaprism finder is removably attached.
Figure 4A:
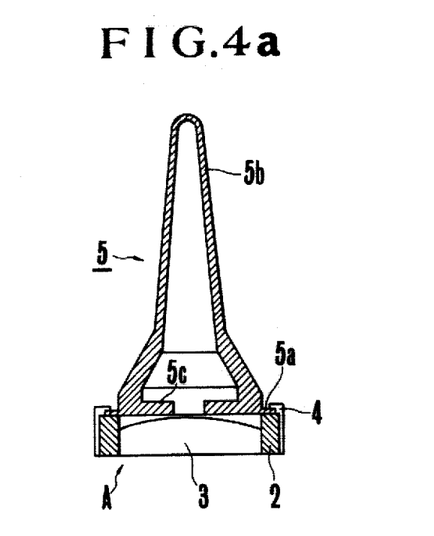
FIG. 4(a) is a sectional view of the focusing screen unit of FIG. 3 carried on the interchanging tool.

In FIG. 3, 1 is a camera housing; 1a is a recessed portion formed in the camera housing 1 under a pentaprism unit (not shown) to accommodate a focusing screen 3 in a fixture member 2. The parts 2 and 3 constitute a focusing screen unit A wherein clamp holder members 4 have their ends provided with pawled portions 4a for engagement with outer side edges 5a of an interchanging tool 5. Again the interchanging tool 5 has a grip 5b and stoppers 5c for protection of the focusing screen 3. With the device of such construction, when the focusing screen unit A is to be attached to and detached from the recessed portion 1a of the camera housing 1, the interchanging tool 5 is brought into engagement at its outer edges 5a with the pawled portions 4a of the clamp holder members 4 and is maintained in the engaged position under the action of an elastic force of the grip 5b as shown in FIG. 4(a). With the help of this tool, it is made possible to take the focusing screen unit A out of the recessed portion 1a of the camera 1 with ease while permitting the camera body 1 to stand upright, no matter how deep the recessed portion is and regardless of the difficulty in achieving access of an operator's finger thereto. Moreover, since at this time the protection stoppers 5c of the interchanging tool 5 are in contact with the upper surface 2' of the focusing screen fixture member 2, but not with the upper surface of the focusing screen 3, provided the upper edge 2' is made higher than the focusing screen 3, there is no possibility of an accidental contact of the engagement portions 5a of the interchanging tool 5 with the focusing screen 3 which might result in scratches. An advantage is, therefore, that the attaching and detaching operation can be speeded up without requiring the camera body to be turned upside down and without the fear of allowing finger prints or stains to adhere to the focusing screen 3, while still permitting an accurate and reliable fitting of the focusing screen unit in the camera body to be achieved.

Figure 4B:
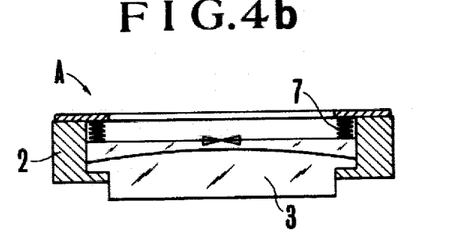
FIG. 4(b) is a cross sectional view showing a modification of the focusing screen unit shown in FIG. 4(a).

Also as shown in FIG. 4(b), when the focusing screen unit A is constituted in such a way that the focusing screen 3 is slidably mounted on the fixture member 2 and at the same time a spring 7 is provided between the focusing screen and the fixture member so as to bias the focusing screen to the camera body 1 when the focusing screen unit A is mounted on the camera body 1, the interchange of the focusing screen can be made more easily because it is possible to float upward the fixture member when the finder prism portion (not shown) is removed for the interchange. Also in this embodiment, the focusing screen 3 is pressed onto the standard surface on the camera side so that there is caused no problem such as loosening and displacement between the standard surface and the focusing screen so that the focusing screen can be attached with a high accuracy.

Figure 5:
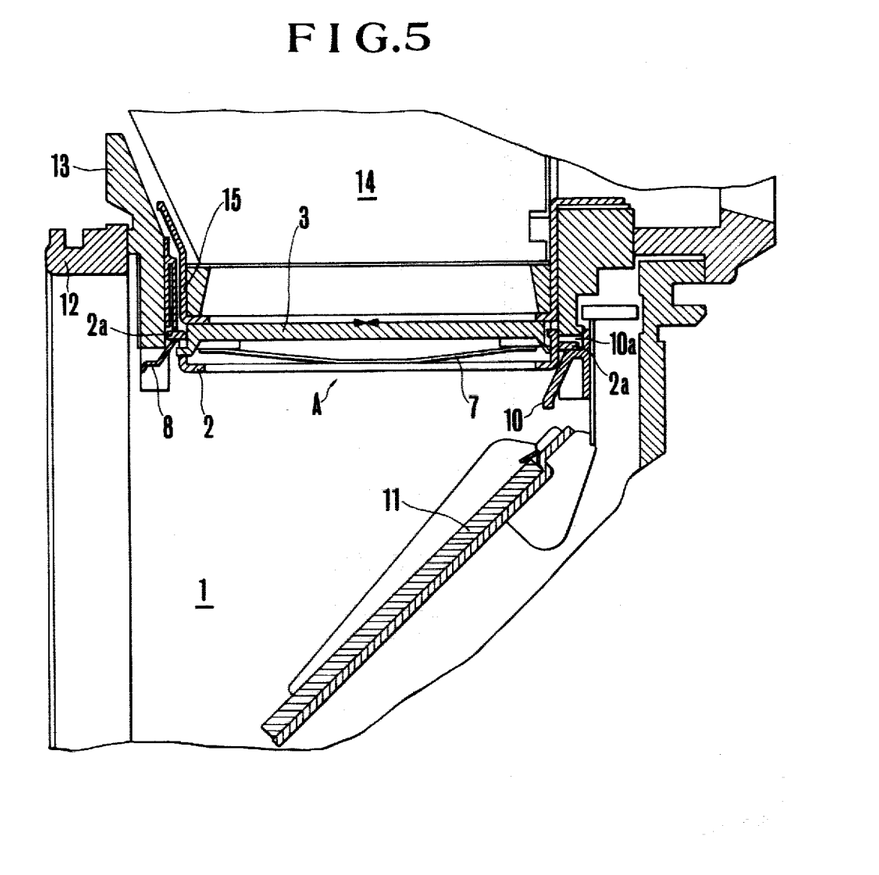
FIG. 5 is a sectional view of another embodiment of the focusing screen interchanging device according to the present invention applied to the type of camera whose focusing screen is dealt with through the opening of the mount for the objective lens.

Next, in FIG. 5, 1 is a camera body; 2 is a fixture member for a focusing screen 3. The member 2 is provided with projected portions 2a on the side walls thereof as shown in the figure. When the focusing screen unit A is attached in a fitted position within the camera housing 1 as shown in FIG. 5, the focusing screen 3 is urged upwards by a leaf spring 7. 14 is a pentaprism; 15 is a frame for the pentaprism 14, against the bottom edge of which is pressed the upper surface of the focusing screen 3 by the spring 7. Thus, the positioning of the focusing screen 3 is adjusted. 10 is a receptor plate for the focusing screen unit A having holes 10a formed therein and arranged to engage the one-side projected portions 2a of the focusing screen fixture member 2. 13 is a front panel of the camera housing 1; and 12 is a mount portion for an objective lens. 8 is a hook which fixedly secures the focusing screen fixture member 2 at the opposite-side projected portion 2a after the latter has been pushed upwards past the hook 8 as the hook 8 has been retracted and then projected again under the action of its own elastic force.

Figure 6A:
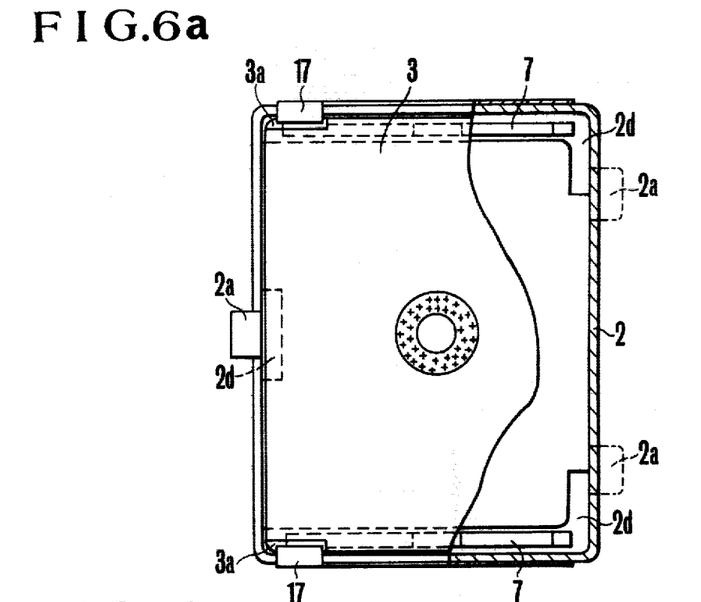
FIGS. 6(a), (b) and (c) are top, side elevational and sectional views respectively of a practical embodiment of the focusing screen unit of FIG. 5.
Figure 6B:
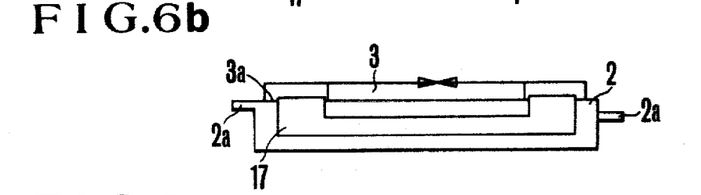
Figure 6C:
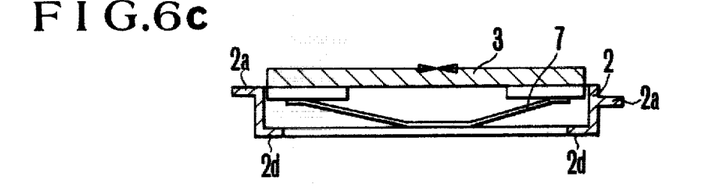

By the way, in FIGS. 6(a), (b) and (c) showing a practical embodiment of the focusing screen unit A in this focusing screen interchanging device, 2a represents projected portions for bearing the focusing screen unit A on the camera body 1; 3 is a focusing screen of which the corners are provided with grooves 3a. Again, 7 is a leaf spring for biasing the focusing screen 3; 17 identifies retainer members upon contact with the grooves 3a of the focusing screen 3 to prevent the focusing screen 3 from being accidentally taken out of the fixture member 2. That is, in this embodiment, the focusing screen 3 is fitted in the fixture member 2 and the leaf springs 7 are incorporated in the fixture member to urge the focusing screen 3 in one direction. And, the retainer members 17 are fastened to the fixture member 2 and acted on the focusing screen 3. Thus, the parts 2 and 3 are assembled in a unit. The focusing screen fixture member 2 is further provided with clamp holder members 2d cooperative with an interchanging tool to be described later, whereby the focusing screen unit A can be interchanged without the necessity of direct contact of operator's fingers thereon.

Figure 7A:
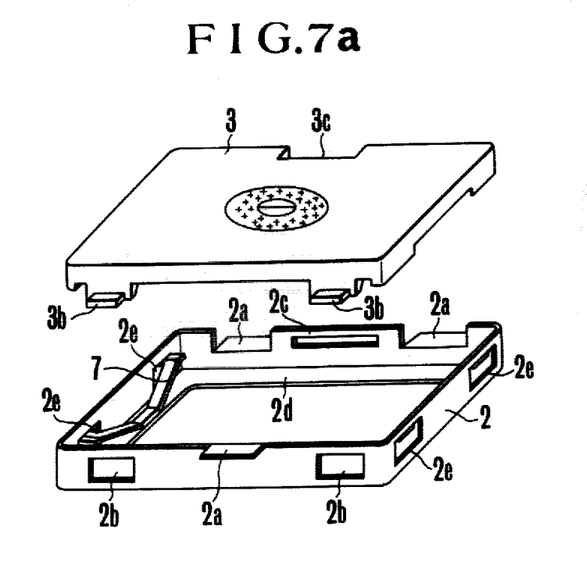
FIGS. 7(a) and (b) are exploded and complete perspective views respectively of another practical embodiment of the focusing screen unit of FIG. 5.
Figure 7B:
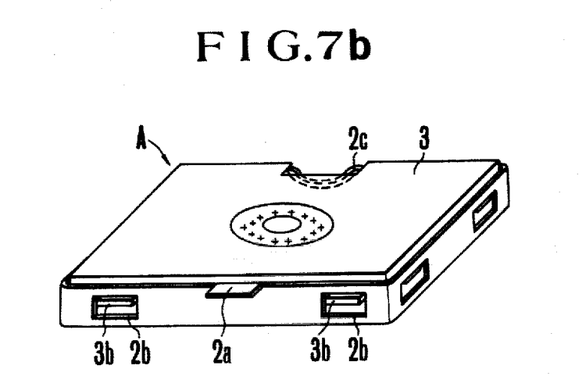
Figure 8A:
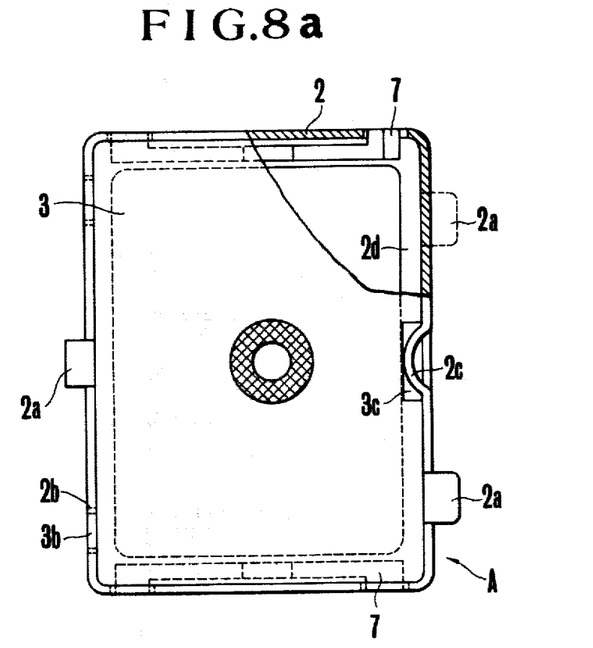
FIGS. 8(a) and 8(b) are top and sectional views respectively showing the assembled state of the focusing screen unit of FIG. 7(b).
Figure 8B:
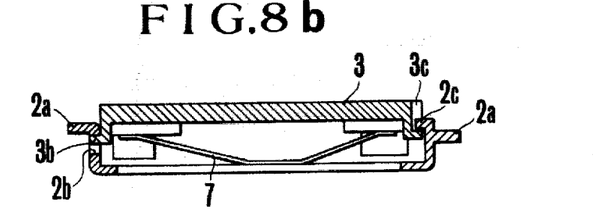

Next, FIGS. 7(a) and (b) and 8(a) and (b) show another embodiment of the focusing screen unit A according to the present invention where the clamp holder portion 2d is so configured and so arranged to reinforce the focusing screen fixture member 2 and to prevent the focusing screen 3 from being affected by an unnecessary stress when out of attachment with the camera body 1. It has been shown that when the focusing screen unit A is attached on the camera body 1 as shown in FIG. 5, as the leaf spring 7 is elastically deformed to exert a force at the coupling and fixedly bearing portions 2a and the leaf spring 7-bearing portions, the focusing screen fixture member 2 is subjected to the corresponding stress and moment. If the focusing screen fixture member 2 is weak, it is caused to deform with the resultant focusing accuracy being made unacceptable. It is, therefore, of importance to provide the fixture member 2 with shoulder portions on the inside surfaces thereof so that the strength of the framework of the fixture member 2 is enhanced. On this account, according to this embodiment, the clamp holder portion 2d is constructed in the integral form over the entire length of the inner periphery of the framework of the fixture member 2, thus functioning as the above-described shoulder portion. Another problem arising from the lack of looseness between the focusing screen 3 and the fixture member 2 when the focusing screen unit A is not in use and is taken out of the camera body 1, is that the constant application of the bias force of the leaf springs 7 on the focusing screen 3 tends to deform the focusing screen 3 which is made of plastics as the environmental factors such as temperature and humidity vary. To solve this problem, according to this embodiment, the focusing screen fixture member 2 is provided with windows 2e in the side walls thereof against the edges of which are abutted the free ends of the leaf springs 7 when the focusing screen unit A is in the idle position, as the focusing screen 3 is freed from the bias force of the leaf springs 7. Further, in this embodiment, the method of assembling the focusing screen 3 and the fixture member 2 therefor in a unit is that either one of the side walls of the focusing screen fixture member 2, which are provided with the projected portions 2a, is provided with windows 2b for coupling with the focusing screen 3, and the opposite side wall is made susceptible to plastic deformation to a curvature convex toward the inside at a portion 2c thereof. And, the focusing screen 3 is provided with projected portions 3b and a cutout 3c to allow for a fine adjustment in vertical position of the focusing screen 3 when assembled in the unit. In the assembling process the projected portions 3b of the focusing screen 3 is inserted into the respective windows 2b in the fixture member 2, and then the opposite side wall at the portion 2c is bent toward the inside. Thus, a unit is produced. At this time, the size of opening of the window 2b and the width of the deformed portion 2c are determined to provide an appropriate looseness between the focusing screen 3 and the springs 7. Such provision of the looseness which takes place to make ineffective the action of the springs 7 when the focusing screen unit A is not in use assures that the focusing screen 3 is not subjected to deformation and in this sense the required focusing accuracy can be always obtained. The further provision of a portion 2c capable of plastic deformation saves production cost which would be otherwise necessary to assemble the unit.

Figure 9A:
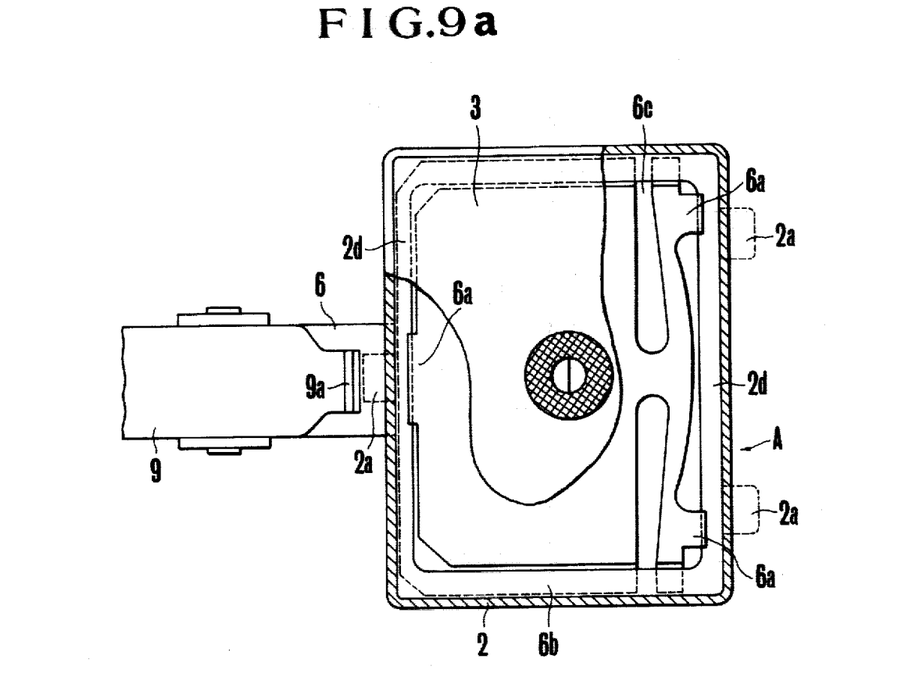
FIGS. 9(a) and (b) are top and side elevational views respectively of the focusing screen unit of FIG. 7(b) carried on an interchanging tool.
Figure 9B:
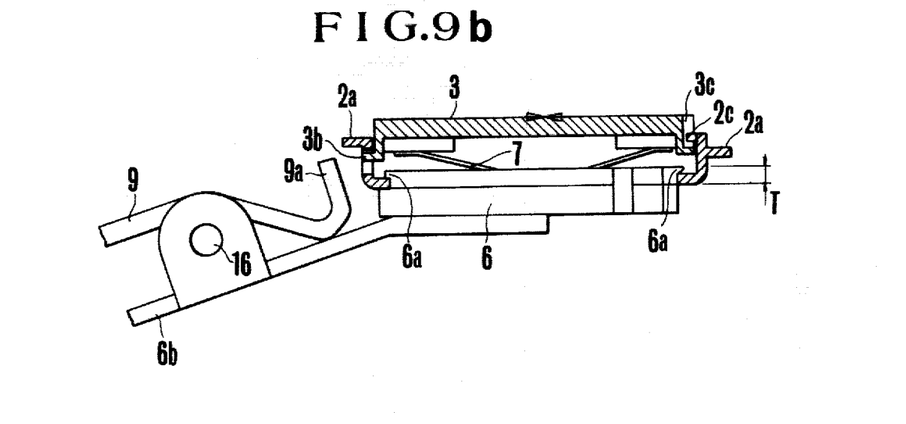
Figure 10A:
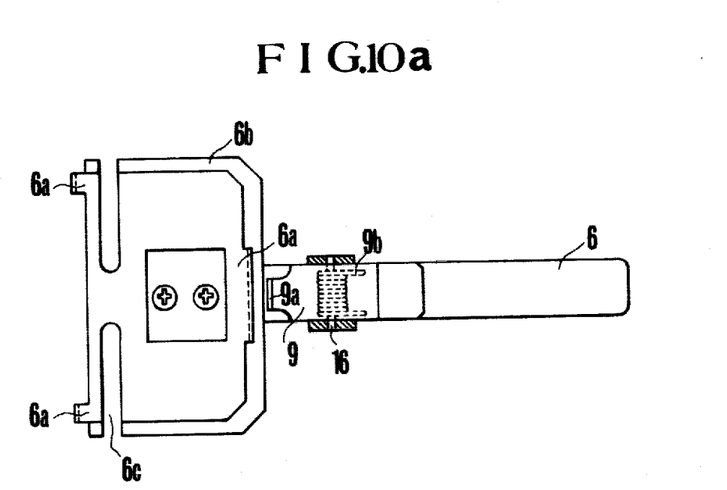
FIGS. 10(a) and (b) are top and side elevational views respectively of a practical embodiment of the interchanging tool according to the present invention.
Figure 10B:
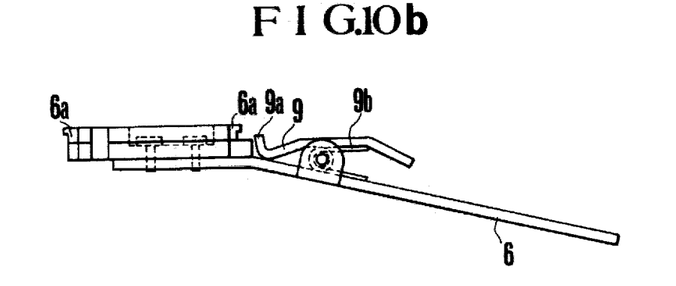

Next, FIGS. 9(a) and (b) show the coupled position of the focusing screen unit A with a member 6 for interchanging operation, and FIGS. 10(a) and (b) show a practical embodiment of this member 6. In the figures, 9 is a lock release lever having a pawled portion 9a for releasing the projected portions 2a of the focusing screen fixing member 2 from the locking connection with a hook 8 when the focusing screen unit A is in attachment on the camera body 1, and urged by a spring 9b to turn about a pin 16 in a clockwise direction as viewed in FIG. 9(b). The interchanging member 6 also has a support surface for the focusing screen unit A provided with a coupling portion 6a at one side thereof which reversibly changes its position by virtue of a resilient property as open slots 6c are formed in the support surface described above. This makes it possible to couple and decouple the portions 6a to and from the clamp holder portions 2d of the focusing screen fixture member 2. A safety holder portion 6b receives the bottom surface of the focusing screen unit A so that the position of the focusing screen unit A relative to the camera body can be controlled so as not to effect an inclined attachment, and the once determined position can be stabilized. Further, the thickness T of the coupling portion 6a is adjusted so that a sufficient space can be created between the focusing screen 3 and the support surface of the interchanging member 6 as shown in the figures when in the coupled position. Thus, it is possible to cause said coupling portions 6a to play the role of a protection stopper for protecting the focusing screen 3 from scratches.

Figure 11A:
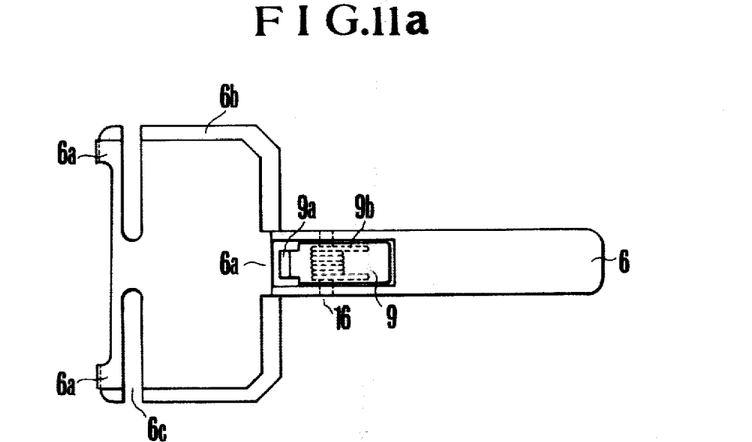
FIGS. 11(a) and (b) are top and partly side elevational partly sectional views respectively of another practical embodiment of the interchanging tool of the type illustrated in FIGS. 10(a) and (b).
Figure 11B:
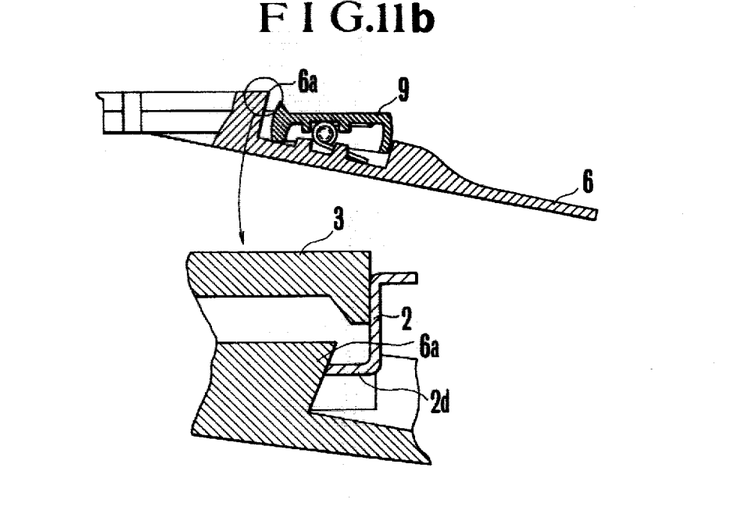

FIGS. 11(a) and (b) are top plan, partly side elevational partly sectional and fragmentary enlarged views showing another practical embodiment of the focusing screen unit interchanging member according to the present invention. In this embodiment the handle 6 of the interchanging member 6 is molded in unison with the carrier plate thereof. Such unified molding provides advantages from the viewpoint of assembly, parts and cost. Further, as shown in the enlarged scale of FIG. 11(b), the lock release lever side coupling portion 6a is tapered so that when the interchanging member 6 is decoupled, the occurrence of violent downward movement instead of normal pushing movement due to misoperation will not lead to damage of the focusing screen unit. It is also noted that such interchanging member 6 may be modified so that the focusing screen unit A is coupled in a lateral direction.

Figure 12A:
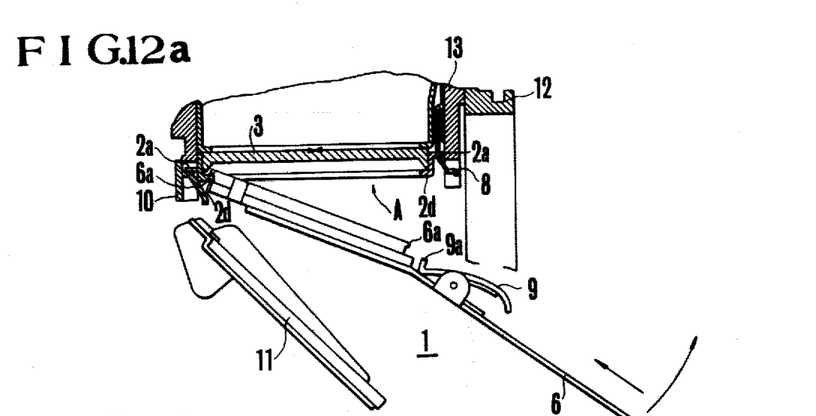
FIGS. 12(a), (b) and (c) are partly sectional partly side elevational views showing a manner in which the focusing screen unit in the focusing screen interchanging device of FIG. 5 is taken out.
Figure 12B:
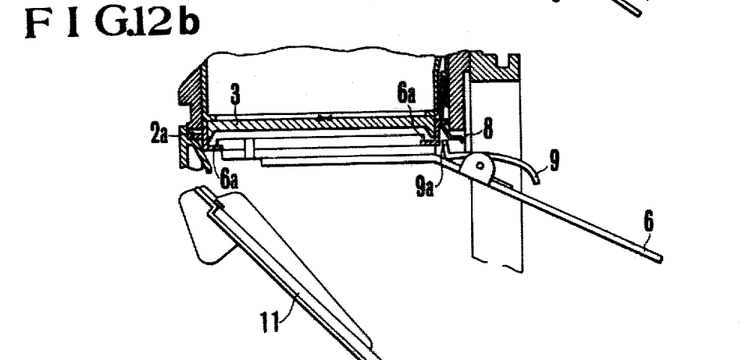

During interchanging operation of the focusing screen interchanging device of such construction to effect removal, as shown in FIG. 12(a), the coupling portion 6a of the front end of the interchanging member 6 is brought into abutting engagement with the clamp holder portion 2d of the focusing screen fixture member 2 of the focusing screen unit A, then while the interchanging member 6 is being pushed in a direction indicated by the arrow, the handle portion is turned about the coupling portion 6a in a counter-clockwise direction until the interchanging member 6 abuts on the bottom surface of the focusing screen fixture member 2. Then, the pushing operation is terminated, whereby the clamp holder portion 2d on the opposite surface of the focusing screen fixture member 2 is automatically engaged with the coupling portion 6a on the opposite surface of the interchanging member 6 under the action of the resilient property of the coupling portion 6a as shown in FIG. 12(b).

Figure 12C:
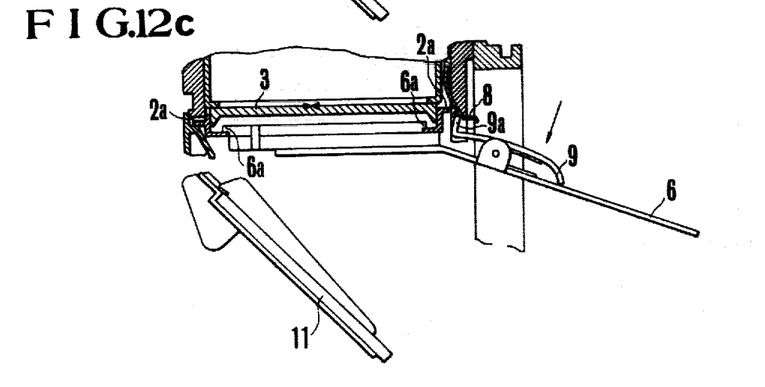

Then, when the lock release lever 9 on the interchanging member 6 is pushed in the direction indicated by the arrow, as shown in FIG. 12(c), the hook 8 of the camera body 1 is deformed by the pawled portion 9a of the lock release lever 9 to disengage from the focusing screen fixture member 2. Though at this time the focusing screen unit A is disengaged from the camera body 1 at the projected portions 2a engaging the receptor plate 10, it is caught by the interchanging member 6 under the action of the resilient property of the clamp holder portion 6a of the interchanging member 6. Therefore, the interchanging member 6 while carrying the focusing screen unit A thereon may be pulled out of the opening of the amount for the interchangeable lens. Thus, without the necessity of picking up the focusing screen unit A directly by fingers of the operator, that is, without causing the focusing screen 3 to be dirtied or scratched, the focusing screen unit A can be detached from the camera body 1.

Figure 13A:
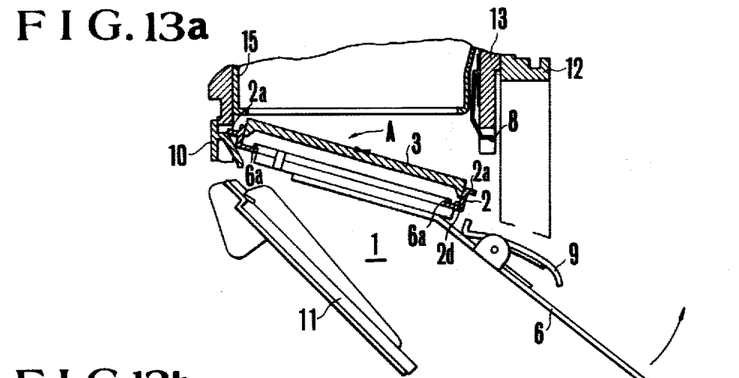
FIGS. 13(a), (b) and (c) are similar views showing a manner in which the focusing screen unit in the focusing screen interchanging device of FIG. 5 is attached.
Figure 13B:
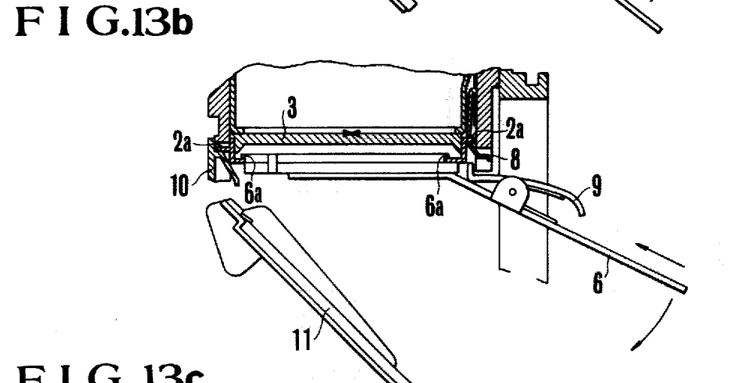
Figure 13C:
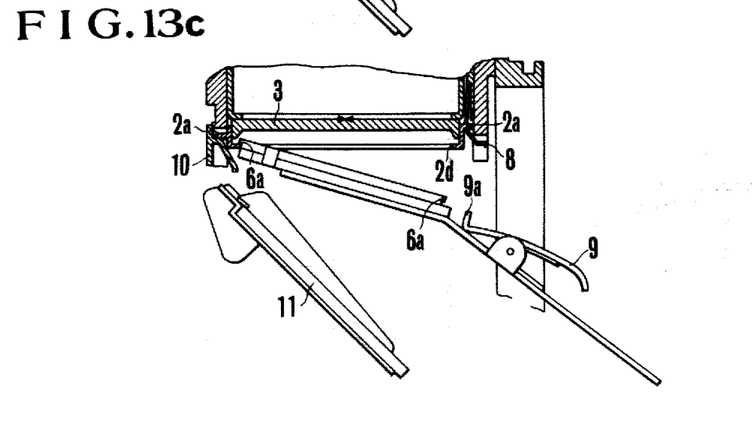

When the focusing screen unit A is to be attached to the camera body 1, as shown in FIG. 13(a), the interchanging member 6 while carrying the focusing screen unit A thereon is inserted through the opening of the mount for the objective lens, and then the projected portion 2b on the far side of the focusing screen fixture member 2 is engaged in the receptor plate 10 in the camera housing 1. At this time, the engagement of the projected portion 2a in the receptor plate 10 can be facilitated by the provision of a guide member (not shown). Then, when the handle is turned about the said projected portion 2a in a counterclockwise direction, the projected portion 2a on the opposite or near side of the focusing screen fixture member 2 is engaged with the hook 8 as shown in FIG. 13(b), whereby the focusing screen unit A is fitted along with the interchanging member 6. After that, the handle of the interchanging member 6 while being pushed in a direction indicated by the arrow is turned about the coupling portion 6a of the interchanging member 6 in the clockwise direction, whereby the interchanging member 6 only is disengaged as shown in FIG. 13(c). At this time, the focusing screen unit is left attached on the camera body 1. Then, the interchanging member 6 is taken out of the mount opening, thus completing the attaching operation of the focusing screen unit A.

Figure 14A:
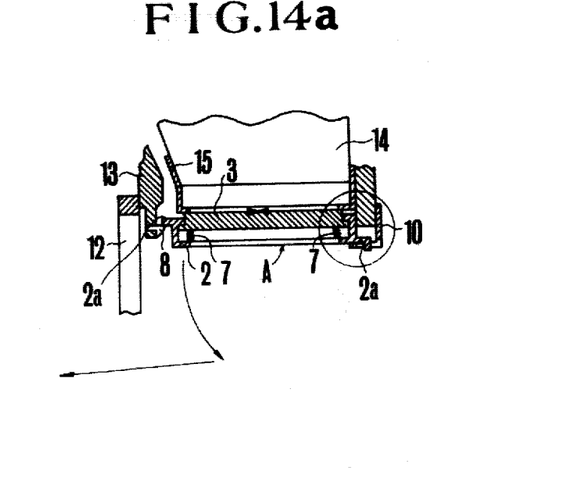
FIGS. 14(a) and (b) are fragmentary sectional views of another embodiment of the focusing screen interchanging device according to the present invention.
Figure 14B:
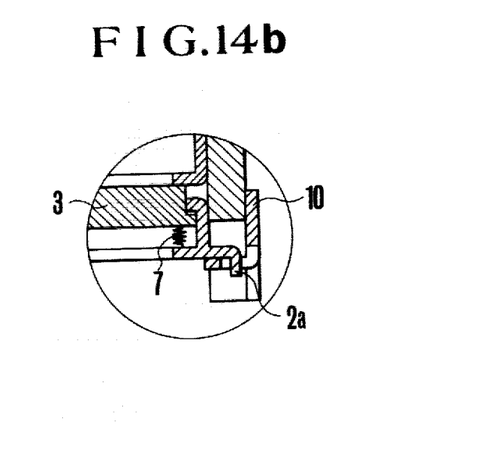

It is also possible to construct the focusing screen interchanging device of the invention as shown in FIGS. 14(a) and (b). That is, as shown in these figures, the spring 7 urging the focusing screen 3 to be pressed with its upper surface against the bottom face of the pentaprism frame 15 when the focusing screen unit A is attached to the camera body 1 may take the form of a coil spring instead of the leaf spring. Further, the structure of the receptor plate 10 provided in the camera body 1 and the projected portion 2a of the focusing screen fixture member 2 may be modified as shown in FIG. 14(b) so that the coupling of both can be made more reliable.

As has been described in greater detail, the present invention is intended to provide a focusing screen interchanging device in which the focusing screen and the fixture member therefor are assembled in a unit, and wherein said focusing screen fixture member is provided with a clamp holder member for coupling with an interchanging tool and which has many advantages as follows:

(1) No possibility of occurrence of finger prints and scratches on the focusing screen due to interchanging.
(2) Prevention of the Up-Down mirror in the camera housing from finger prints, stains and scratches.
(3) Easy establishment of the required accuracy of adjustment in position of the focusing screen since the fixture member for the focusing screen is not inherently mounted in, or freed from, the framework of the camera body.
(4) Possibility of accurately interchanging the focusing screen and simplicity of procedure.
(5) No necessity of disassembling the camera body even when the focusing screen fixture member is damaged, and therefore no fear of failure of re-establishment of the accuracy after the disassembly.
(6) Good protection of the focusing screen and focusing screen unit from damages since the clamp holder member of the focusing screen fixture framework for cooperation with the interchanging tool also serves to reinforce the focusing screen fixture framework.
(7) Low cost because the assembling of the focusing screen to a unit is performed by the plastic deformation.
(8) No deviation of the accuracy due to the deformation of the focusing screen since the bias force of the spring is taken out of the focusing screen when not in use.

While specific embodiments of the invention have been shown and described in detail to illustrate the application of the inventive principles, it will be understood that the invention may be embodied otherwise without departing from such principles.

What is claimed is:

1. A focusing screen interchanging device in a single lens reflex camera of the type in which the finder-pentaprism portion of the camera body is made fixed, comprising:
   a focusing screen;
   a fixture member for fixing the focusing screen to the camera body, said fixture member and said focusing screen being united together and having a spring therebetween for energizing said focusing screen;
   an interchanging tool member for interchanging the focusing screen through an opening of a mount for an interchangeable lens of the camera housing, said interchanging tool being capable, upon coupling from the bottom, of carrying the focusing screen through the fixture member;
   a coupling member for coupling the interchanging tool member to the fixture member, said coupling member being provided in the fixture member; and
   holding means for holding the fixture member in the camera body, said holding means being provided in the camera body.

2. A device according to claim 1 wherein the fixture member has a spring abutment for preventing the bias force of the spring member from acting on the focusing screen when the fixture member is detached from the camera body.

3. A device according to claim 1 or claim 2, wherein the holding means has a resilient engagement member for engaging and holding the fixture member.

4. A device according to claim 3, wherein the interchanging tool member has a release member for releasing the engagement of the fixture member with the resilient engagement member.

5. A focusing screen interchanging device in a single lens reflex camera comprising:
   a focusing screen;
   a fixture member for fixing the focusing screen to a camera body, said fixture member being united together with the focusing screen and holding the focusing screen in a freely shiftable manner at its inside, said fixture member being further provided in a manner freely attachable to and detachable from the camera;
   biasing means to bias the focusing screen, said biasing means being provided at the fixture member;

a standard member provided at the camera body, the focusing screen being pressed against said standard member by the bias force of the biasing member when the fixture member is fixed with the camera body; and holding means for holding the fixture member within the camera body, said holding means being provided in the camera body.

6. A device according to claim 5 which further comprises an interchanging tool capable, upon coupling, of carrying the focusing screen through the fixture member when interchanging the focusing screen.

7. A device according to claim 6 wherein the interchanging tool is engaged with a bottom part of the fixture member, and has an operating part extended to an obliquely downward direction from a part at which the fixture member is engagingly held.

8. A device according to claim 6 wherein the interchanging tool is engaged with an upper part of the fixture member and has an operating part extended upwardly from a part at which the fixture member is engagingly held.

9. A device according to claim 7 or 8 wherein the interchanging tool is elastically connected to the fixture member.

10. A device according to claim 8 wherein a finder-pentaprism of the camera body is provided in a manner freely attachable to and detachable from the camera body.

* * * * *